United States Patent [19]

Häberlein

[11] 4,270,089
[45] May 26, 1981

[54] SCANNING MAGNETIC TEST HEAD

[75] Inventor: Peter Häberlein, Reutlingen, Fed. Rep. of Germany

[73] Assignee: Samsonite Corporation, Denver, Colo.

[21] Appl. No.: 945,681

[22] Filed: Sep. 25, 1978

[30] Foreign Application Priority Data

Oct. 7, 1977 [DE] Fed. Rep. of Germany ....... 2745159

[51] Int. Cl.³ ..................... G01R 33/00; F16H 19/06; F16H 37/00
[52] U.S. Cl. ................................. 324/262; 324/228; 74/37
[58] Field of Search ........ 324/200, 228, 234, 236–240, 324/262; 74/37

[56] References Cited

U.S. PATENT DOCUMENTS

| 2,224,431 | 12/1940 | Heginbotham et al. ................ 74/37 |
| 2,388,683 | 11/1945 | Frickey et al. ....................... 324/217 |
| 2,617,854 | 11/1952 | Van Valkenburg ................ 324/240 |
| 3,281,667 | 10/1966 | Dobbins et al. . |
| 3,617,875 | 11/1971 | Mandula et al. . |
| 3,673,876 | 7/1972 | Rohner ..................................... 74/37 |
| 4,088,034 | 5/1978 | Wallis ..................................... 74/37 |
| 4,118,993 | 10/1978 | Miyoshi et al. ......................... 73/37 |

FOREIGN PATENT DOCUMENTS 2051987 3/1971 France .

Primary Examiner—Gerard R. Strecker
Assistant Examiner—Walter E. Snow
Attorney, Agent, or Firm—George J. Netter

[57] ABSTRACT

A scanning test head is provided which maintains a constant speed over the scanning path with the constancy of the speed in the scanning zone being dependent solely on the drive motor characteristics. An endless belt received on a pair of spaced rollers carries a pin which, on being driven around the closed path, serves to define the head scanning path.

8 Claims, 6 Drawing Figures

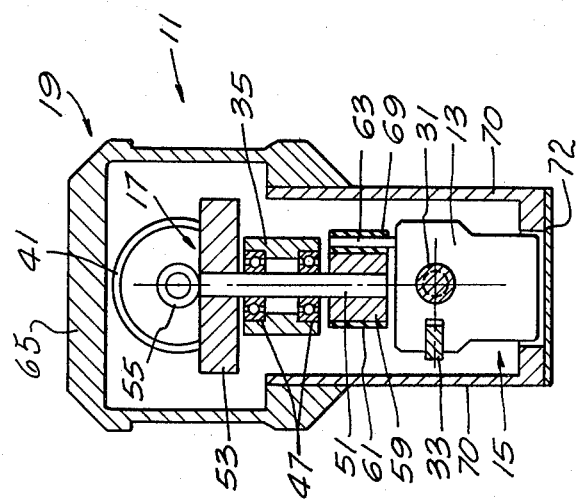
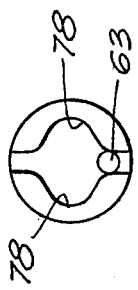
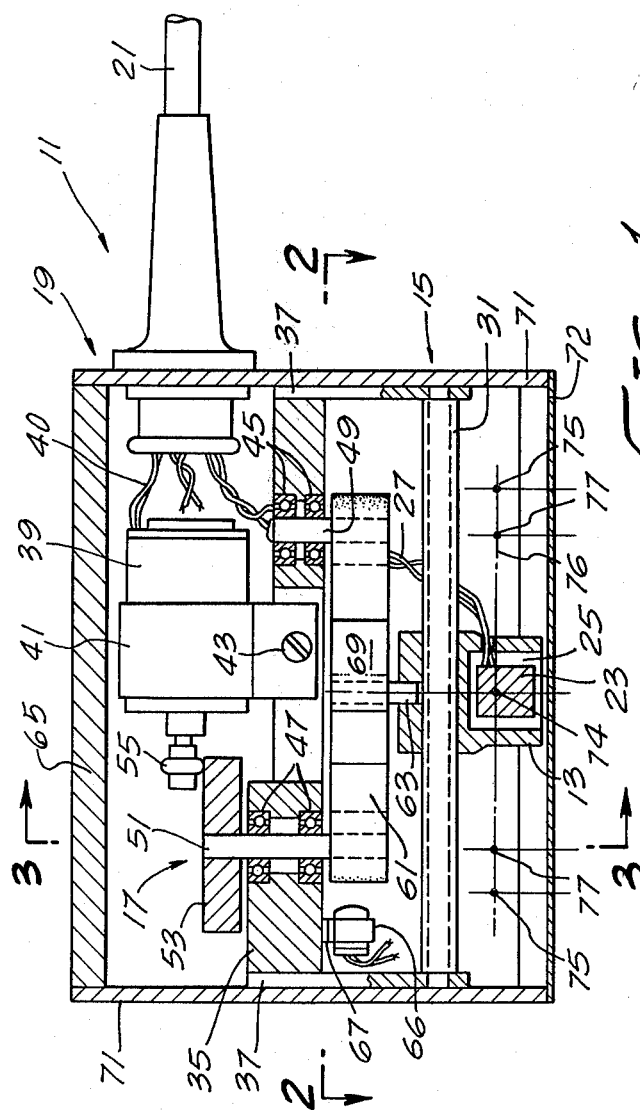
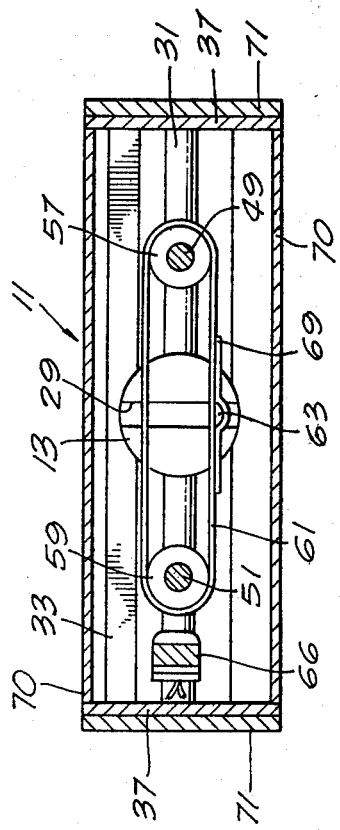

SCANNING MAGNETIC TEST HEAD

The present invention relates generally to a magnetic test head for use in nondestructive material testing, and, more particularly, to such a test head adapted for scanning movement relative to a surface of the material being tested.

BACKGROUND OF THE INVENTION

Test heads of the scanning type have been long known in different forms in the field of nondestructive testing of materials, in particular for testing the surfaces of semifinished products. U.S. Pat. No. 3,281,667, shows an arrangement in which a test probe mounted at the top end of a lever is reciprocated as a result of the other end of the centrally mounted lever being connected to a cam. Also, U.S. Pat. No. 3,469,182 describes a probe bar with a number of test probes to which an oscillating movement is imparted by cam action at its two ends.

A first disadvantage of the arrangements described in the referenced patents, is to be seen in the curved movement paths of the probes, which can be avoided in a relatively simple manner by the use of corresponding guides. However, a more serious disadvantage is that the speed of the oscillating movement exhibits a sinusoidal variation between zero and the maximum value, and has only a very small constant zone. It has been found that this variability of oscillating speed proves particularly disadvantageous for electrical processing, i.e., the filtering of the signal voltage of the probe. Due to the varying speed of the probes, an excessively large bandwidth for the filter is required, which, in turn, has a detrimental effect on the signal-to-noise ratio of the signal voltage.

From U.S. Pat No. 3,311,819 an arrangement for testing billets is known which permits a scanning movement of essentially constant speed over a predetermined area, i.e., the billet width. In this case, the oscillating movement is imparted to the test probe by the piston of a hydraulic jack which changes its direction of movement when a sensing element signals that the billet edge has been reached by the probe support. A disadvantage of this arrangement lies in the high cost, the necessity of a hydraulic supply line, and the relatively large dimensions of such an arrangement.

SUMMARY OF THE INVENTION

In accordance with this invention a scanning test head is provided which maintains a constant speed over the scanning path.

This arrangement enables in a very simple manner the zone of constant speed to be fixed at practically any desired length, since the latter corresponds to the center distance spacing of the two guide roller bodies. Also, the constancy of the speed in the zone is merely dependent on the drive motor used. The construction may be made extremely compact, and this in turn makes the test head of the invention suited for a large range of applications. When appropriately designed, even extremely high oscillating speeds may be obtained without any difficulty, and this in turn permits a rapid advance movement of the test head in vertical relation to the path of the oscillating movement resulting in high testing speed.

DESCRIPTION OF THE DRAWING

FIG. 1 shows a cross-sectional view of a hand scanner and test head.

FIG. 2 is a sectional view taken along the line 2—2 of FIG. 1.

FIG. 3 is another sectional view taken along the line 3—3 of FIG. 1.

FIG. 4 is an alternative detail.

DESCRIPTION OF PREFERRED EMBODIMENTS

Figure 5:
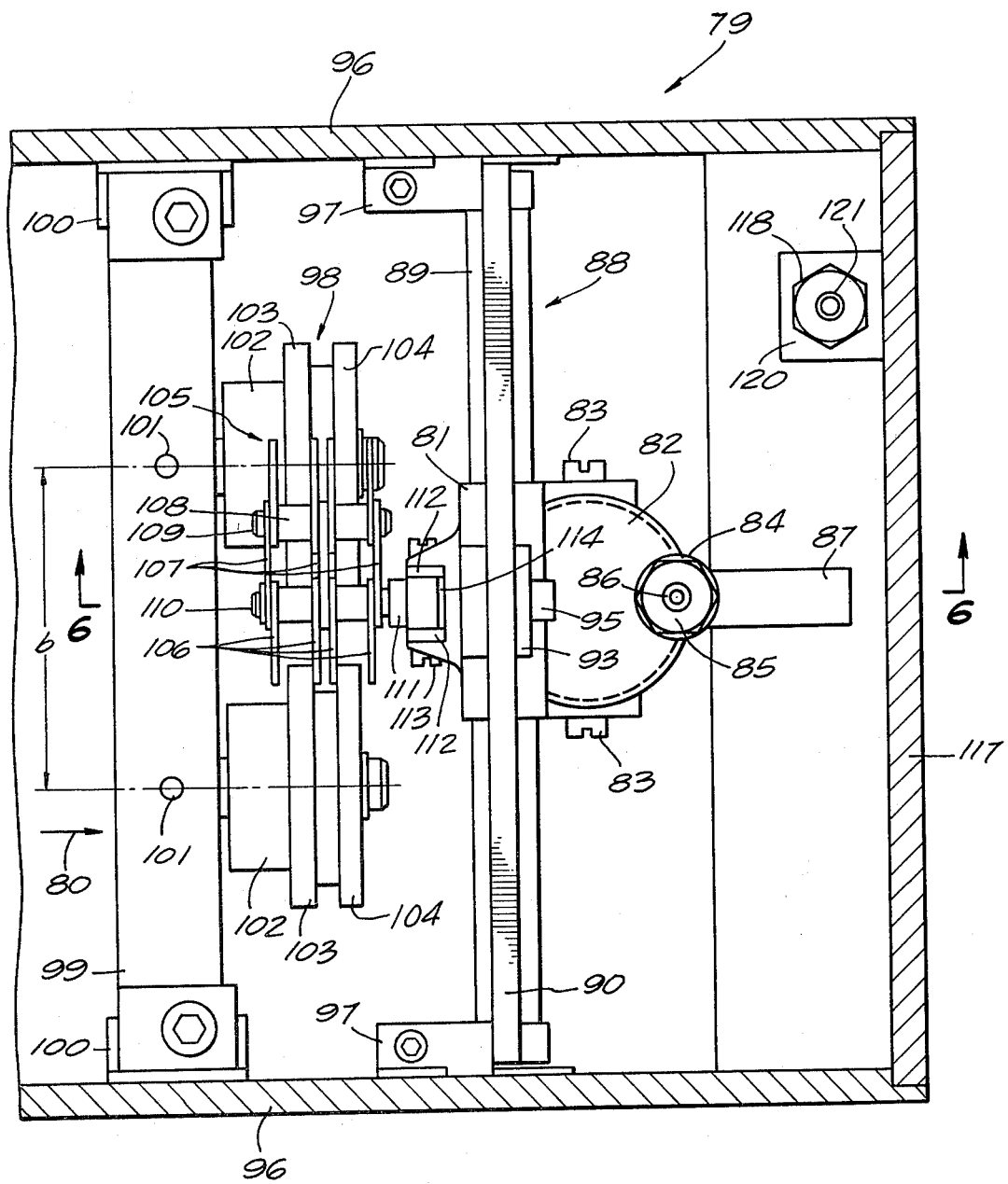
FIG. 5 shows a test head for testing slablike workpieces.

FIGS. 1 to 3 show different cross-sections through a hand held scanner, which is one application of the test head of the invention. In this context, a hand scanner is seen to be a scanner having test probes, in particular eddy-current probes, which are moved by hand over the surface of a part under test. Such test scanners in the past have been equipped with rigidly mounted probes, but lately they have also been equipped with probes revolving along a circular path, which are especially advantageous for testing the shaft of boreholes, for example. In the present case, the probe oscillates along a straight path permitting the manual execution of material tests on large surfaces, which is of particular interest for routine tests of components in the aeronautical engineering field.

The hand scanner includes the following main assemblies: A support 13, guide means 15, drive means 17, a housing 19, and a connecting cable 21. The support 13 has a test probe 23 embedded in a bore 25 which is connected to the cable 21 by conductor leads 27. The upper surface of the support 13 is provided with a groove 29 (FIG. 2) extending in crosswise direction relative to its direction of movement. The support 13 is guided by guide means 15, the latter including cylindrical rod 31 and a bar 33 of rectangular cross-section. The rod 31 and the rectangular bar 33 are guided within a bore and groove, respectively, in the support 13. The individual components of the drive means 17 are arranged on a beam 35 mounted between two steel plates 37 which also carry the cylindrical rod 31 and the rectangular bar 33 of the guide means 15. A drive motor 39 with connecting wires 40 is mounted to the beams 35 by means of a bracket 41 and screw 43. Further, bearings 45 and 47 are mounted in the beam to journal the shafts 49 and 51, respectively.

The shaft 51 is driven by motor 39 via a spur gear 53 and a driving gear 55. The lower ends of shafts 49 and 51 carry guide rollers 57 and 59 with an endless, textile-reinforced drive belt 61 mounted thereon. A pin 63 is arranged on the outer periphery of the driving belt 61, vertically to the direction of movement of the belt. The connection between the pin and the driving belt 61 is ensured by a strip 69 connected to the driving belt in a suitable manner, for instance by gluing or vulcanizing. The pin 63 extends beyond the side edges of driving belt 61, and its lower portion engages the groove 29 in the support 13. A sensing element 66 mounted in a bracket 67 opposite the guide roller 59 has its connecting wires 68 connected to the cable 21. The sensing element 66 consists of a magnetic head which emits a synchronizing pulse each time it is passed by the pin 63, the latter having been magnetized for this purpose.

The components of the hand scanner 11 are protected and enclosed by housing 19 including a shell 65, two shell plates 70, two end plates 71 (FIG. 2) and a bottom plate 72. Since the latter is to be penetrated by the alternating magnetic field of the test probe 23, it is of reduced thickness and made from a material exhibiting poor magnetic and electric conductivity, as for instance austenitic steel. The cable 21 is fastened to the plate 71 of the housing 19 by means of a wall socket. It provides for the electric connection of the drive motor 39, the test probe 23 and the sensing element 66 with the control and evaluation apparatus not shown in the drawing.

The function of the hand scanner 11 is as follows: The motor 39 drives the guide roller 59 at a speed that has been reduced by the gears 53 and 55 at a ratio of approximately 6:1. The drive belt 61 revolves at a frequency of approximately 10 Hz imparting to the support 13, via the pin 63 engaging the groove 29, an oscillating movement of the same frequency moving the point 74 of the support to and fro between the final points 75 along a path 76. Between the intermediate points 77, the distance of which corresponds to the distance between centers of the guide rollers 57 and 59, the speed of the oscillating movement remains precisely constant, while a sinusoidal variation of the speed is encountered between the points 75 and 77.

In many applications, it may be desirable to suppress the signal emitted by the test probe 23 in the short zones in which the speed shows a sinusoidal variation. This can be easily achieved by providing a switch in the transmission path which is controlled by the revolving cycle of the drive belt 61. To this end, one could for instance provide two sensing elements at the points 77 on both sides of the drive belt 61, to emit pulses when the pin 63 passes. The pulse emitted by the first sensing element could interrupt the transmission path by means of this switch, while the pulse of the second sensing element could close it again. In the present example, the control of such a switch may be achieved by known electronic means. In this case, it will suffice to provide one sensing element 66, the signal of which will synchronize the pulse sequence with the revolving frequency of the drive belt 61.

FIG. 4 shows an alternative design of the groove 29 in the upper surface of the support 13. In the case of the straight groove 29 described earlier herein, the path along which the support 13 moves between the points 75 and 77 corresponds to the radius of the movement of the pin 63, i.e., approximately the radius of the guide rollers 57 and 59. The "dead" path between the points 75 and 77 which is not utilized for scanning may be shortened by causing the pin 63 to slide along a curve 78 instead of a straight groove 29, which curve 78 has only its endmost portions extending in vertical relation to the path 76, whereas the central area exhibits a curvature essentially identical to that of the two guide rollers 57 and 59.

Figure 6:
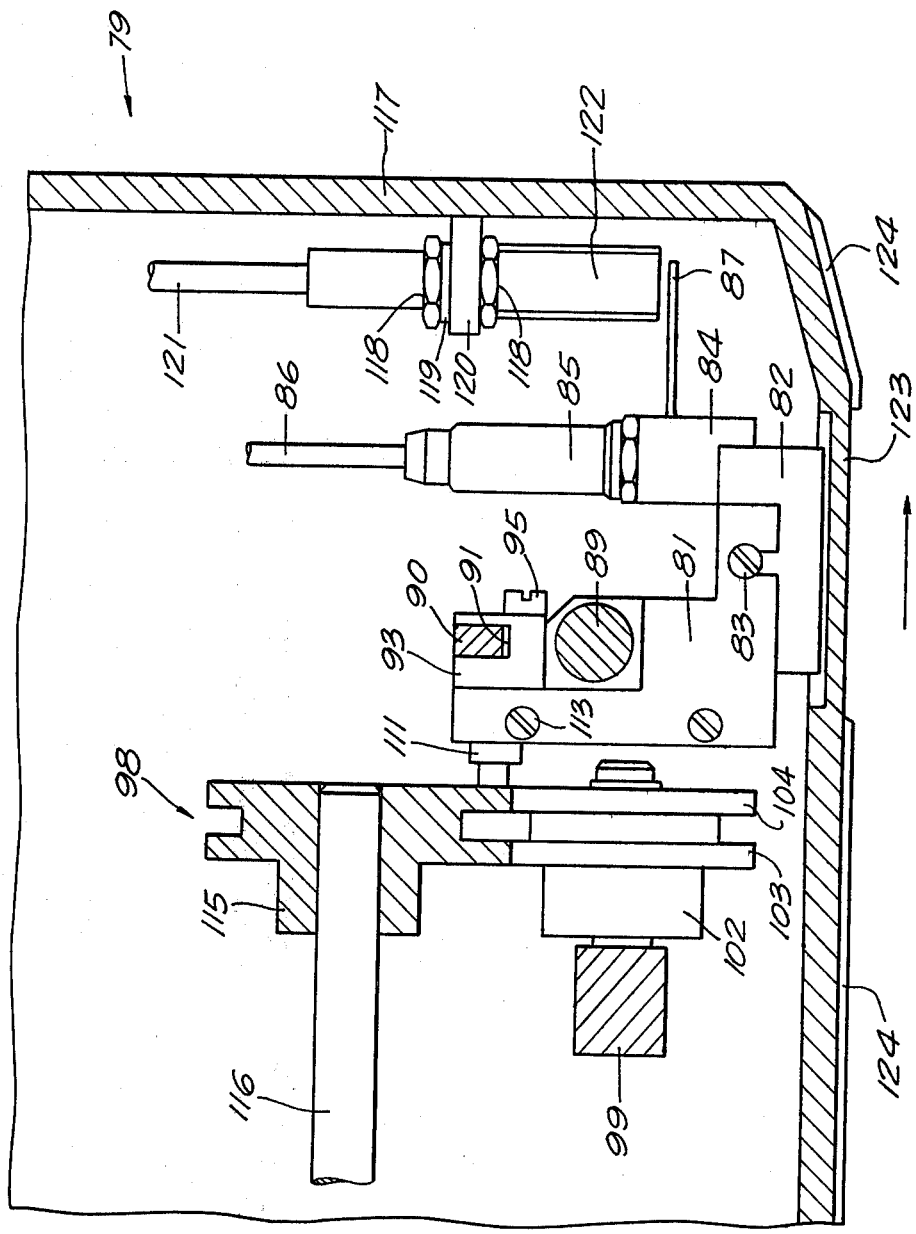
FIG. 6 shows a sectional view of the test head of FIG. 5 taken along the line 6—6.

FIGS. 5 and 6 show two cross-sectional views through a test head 79 which is intended for testing slabs and which forms part of a system for the complete scanning of the surface of a slab. In this arrangement the test head 79 serves to scan a portion of the width b while sliding along the slab surface in the direction indicated by arrow 80. In a circular opening provided in the support 81 of the test head 79, a probe body 82 is fastened by screws 83, which body encloses a further test probe (not shown). The probe body 82 is shielded against possible interference fields by means of a thick copper jacket. A pipe 84 is soldered to the probe body, led through a cable outlet 85 and ends in cable 86. Mounted to this pipe 84 is a steel plate 87. The support 81 is guided by guide means 88 consisting of cylindrical rod 89 and a rectangular bar 90, the latter guided in a groove 91 of a U-shaped bar 93 mounted to the support 81 by means of a screw 95. The cylindrical rod 89 and rectangular bar 90 are connected to the housing walls 96 by means of mounting angles 97. Drive means 98 are mounted to a supporting rail 99 which is fastened to the housing walls 96 by means of angles 100. Two shafts are rigidly fixed at the supporting rail 99 by pins 101. On these shafts, two sprocket wheels 102 with two gear rims 103 and 104 each are seated in bearings (not shown). The said gear rims 103 and 104 engage a double chain 105 of which only a few links are shown for the sake of simplicity.

The individual chains of the double chain 105 are of usual design and equipped with inner side bars 106, outer side bars 107, sliding rollers 108 and connecting shafts 109, the connecting shafts 109 and one outer side bar 107, being common to both individual chains. An extension of the connecting shaft 110 at one side thereof carries a cylinder head 111 through which it imparts to the support 81 the required oscillating movement. The suspension of the connecting shafts 110 on the described double chain 105 considerably increases its capability of transmitting forces in the direction of the guide means 88. The cylinder head 111 slides between two hardened rails 112 fastened by means of screws 113 in a transverse groove 114 in the support 81.

The transmission of forces to the double chain 105 is effected by means of an additional sprocket wheel 115 (FIG. 6) engaging the links of the double chain from above. The sprocket wheel 115 is driven via a shaft 116 through a geared motor not shown in the drawing. A proximity sensor which is mounted on the housing 117 by means of nuts 118, a washer 119 and a shoe 120 and which is connected to the corresponding electronic control unit via a cable 121 serves for generating the synchronizing pulses. A synchronizing pulse is emitted each time the steel plate 87 comes into engagement with the proximity sensor 122 when the support 81 reaches its final position. In the area opposite the path of the probe body 82, the bottom of the housing 117 shows a portion 123 of reduced cross-section which improves the response of the test probe. At the bottom of the housing 117, sliding ribs 124 are provided which are discontinued in the area opposite the path of the probe body 82, so as to prevent pseudo defect indications. The function of the test head 79 is fully analogous to that of the test head in the previously described hand scanner 11.

What is claimed is:
1. A magnetic test head having a support carrying at least one test probe, guide means defining a path of movement for said support, and a drive means, comprising:
   an endless belt mounted on a pair of spaced guide rollers;
   means interconnecting at least one of said guide rollers to said drive means;
   pinlike means carried by said belt and interacting with said support for reciprocating said support and test probe along said path of movement for scanning the surface of an article to be tested, said pinlike means being magnetized and cooperating with a sensing element mounted adjacent the path of movement on moving therepast to generate a signal sequence in synchronism with the belt frequency of revolution; and a housing having walls enclosing and supporting the test probe, guide means, endless belt, interconnecting means and pinlike means, said housing including a bottom plate for contacting the surface of an object to be tested spaced from said test probe, guide means, endless belt, interconnecting means and pinlike means constructed of a material having relatively poor electrical conductivity and magnetic properties.

2. A test head as in claim 1, in which said support includes a groove extending transversely of the centerline of the guide rollers within which the pinlike means is received.

3. A test head as in claim 2, in which said groove extends in a straight line substantially vertically to the guide rollers centerline.

4. A test head as in claim 2, in which the groove has defining walls with straight outer end portions and curved intermediate portions.

5. A test head as in either of claims 1 or 2, in which the drive means is interconnected to the guide rollers via stepdown gearing.

6. A test head as in claim 1, in which said housing is adapted for handheld use.

7. A test head as in claim 1, in which said endless belt and guide rollers comprise closed loop chain means receiving on a pair of rotatably mounted sprocket wheels;

a shaft interconnected with said chain for movement therewith, an end portion of said shaft engaging the support for moving the same along the path of movement.

8. A test head as in claim 7, in which said chain means includes a pair of chains each having inner side bars, outer side bars, sliding rollers and connecting shafts, the connecting shafts and one outer bar being in common for both chains, and one connecting shaft end extending outwardly to engage and move the support along the path of movement.

* * * * *

UNITED STATES PATENT OFFICE
CERTIFICATE OF CORRECTION

Patent No. 4,270,089                Dated May 26, 1981

Inventor(s) PETER HÄBERLEIN

It is certified that error appears in the above-identified patent and that said Letters Patent are hereby corrected as shown below:

First page, line [73], change "Samsonite Corporation, Denver, Colo." to --Institut Dr. Friedrich Förster, Prüfgerätebau--

Signed and Sealed this

Twenty-second Day of September 1981

[SEAL]

Attest:

Attesting Officer

GERALD J. MOSSINGHOFF

Commissioner of Patents and Trademarks